United States Patent [19]

Bertics et al.

[11] Patent Number: 5,516,762
[45] Date of Patent: * May 14, 1996

[54] METHOD OF TREATING ENDOTOXIN EFFECTS WITH 2-HALOADENOSINE NUCLEOTIDE ANALOGS

[75] Inventors: Paul J. Bertics, Oregon; Richard A. Proctor, Madison, both of Wis.

[73] Assignee: Wisconsin Alumni Research Foundation, Madison, Wis.

[ * ] Notice: The portion of the term of this patent subsequent to Oct. 15, 2013, has been disclaimed.

[21] Appl. No.: 137,685

[22] Filed: Oct. 15, 1993

Related U.S. Application Data

[63] Continuation-in-part of Ser. No. 976,659, Nov. 16, 1992, abandoned, which is a continuation of Ser. No. 681,036, Apr. 5, 1991, abandoned.

[51] Int. Cl.$^6$ ........................ A61K 31/70; C07H 19/167
[52] U.S. Cl. ............................................. 514/47; 514/921
[58] Field of Search ............................... 514/46, 47, 921; 536/27.63

[56] References Cited

U.S. PATENT DOCUMENTS

| | | | |
|---|---|---|---|
| 3,678,162 | 7/1972 | Maguire et al. | 514/47 |
| 3,752,805 | 8/1973 | Maguire et al. | 536/27.11 |
| 3,860,706 | 1/1975 | Ikeda et al. | 514/47 |
| 4,826,823 | 5/1989 | Cook et al. | 514/46 |
| 4,918,061 | 4/1990 | Raetz et al. | 514/62 |

OTHER PUBLICATIONS

Lehninger, Albert, "Biochemistry: The Molecular Basis of Cell Structure and Function"; Second Edition, Worth Publishers, Inc. (New York), p. 218.
Tanke et al. Abstract–1989 ASCB Meeting.
Tanke et al. Abstract–30th ICAAC Meeting in Atlanta, Georgia In Oct. 1990.
Tanke et al. article titled "Lipid X inhibition of bacterial lipopolysaccharide–stimulated GTP–ase activity"–Cellular and Molecular Aspects of endotoxin reactions, A. Nowotny et al., Editors, pp. 227–237 (1990).
Lehninger, Albert. Biochemistry: "The Molecular Basis of Cell Structure and Function"; Second Edition, Worth Publishers, Inc. (New York), p. 730.
Sigma Chemical Catalog, 1992, pp. 676–677.
Gough et al. article titled "Three New Adenosine Triphosphate Analogs: Synthesis and Effects on Isolated Gut", Journal of Medicinal Chemistry, 1973, vol. 16, No. 10, pp. 1188–1190.

*Primary Examiner*—Gary L. Kunz
*Attorney, Agent, or Firm*—Quarles & Brady

[57] ABSTRACT

A method of treating a mammal exposed to endotoxin in order to reduce the detrimental effects of said endotoxin, comprising administering to said mammal a therapeutically effective amount of a 2-halo-adenosine nucleotide analog. 2-Cloro-ATP is the preferred species of the 2-halo-adenosine nucleotide. The nucleotide used in this treatment inhibits lipo-polysaccharide-induced GTPase activity.

3 Claims, No Drawings

METHOD OF TREATING ENDOTOXIN EFFECTS WITH 2-HALOADENOSINE NUCLEOTIDE ANALOGS

This invention was made with United States Government support awarded by the National Institutes of Health (NIH), Grant No. RO1 CA47881. The United States Government has certain rights in this invention.

The present application is a continuation-in-part of our U.S. patent application Ser. No. 07/976,659, filed Nov. 16, 1992, now abandoned, which is a File Wrapper Continuation of our earlier U.S. patent application Ser. No. 07/681,036, filed Apr. 5, 1991, now abandoned.

FIELD OF THE INVENTION

The present invention relates to purine analogs. More particularly, it relates to halogen substituted purine analogs and a method employing the analogs to inhibit or prevent the lethal effects of endotoxin.

BACKGROUND OF THE INVENTION

Gram-negative septic shock, which is characterized by a high mortality rate and is responsible for thousands of deaths annually, appears to result from a cascade of events triggered by the action of bacterial endotoxin.

Endotoxin is a lipopolysaccharide (LPS) which is a major constituent of the outer-leaflet of the membranes of Gram-negative bacteria. Structural studies have shown that it consists of the following three distinct domains: 1) the 0-antigen region, which is a strain-specific polysaccharide moiety and determines the antigenic specificity of the organism; 2) the core region, which is relatively conserved with respect to its sugar composition and may play a role in maintaining the integrity of the outer membrane; and 3) the lipid A region, which is also conserved and functions as a hydrophobic anchor holding lipopolysaccharide in place. The lipid A portion of lipopolysaccharide constitutes most of the outer monolayer of the outer membrane in Gram-negatives.

Lipopolysaccharide is known to trigger many pathophysiological events in mammals, either when it is injected or when it accumulates due to Gram-negative infection. In general, the hydrophobic lipid A moiety is responsible for these pathophysiological effects, which tend to be either immunostimulatory or toxic. In the former category there are events such as B-lymphocyte mitogenesis, macrophage activation, and the induction of tumor necrosis in certain experimental systems. In the latter (toxic) category there are responses such as peripheral vascular collapse ("endotoxic" or septic shock), pulmonary hypertension, pulmonary edema, disseminated intravascular coagulopathy and pyrogenicity.

Of particular importance concerning the lethal effects of LPS is the observation that nanogram quantities of LPS can induce the release of mediators such as tumor necrosis factor-α, (TNF-α) interleukin-1 (IL-1), and interleukin-6 (IL-6). The release of mediators such as tumor necrosis factor-a (TNF), interleukin-1 (IL-1), and interleukin-6 (IL-6) is thought to produce the toxicity associated with endotoxemia. However, despite the high mortality rate of endotoxic shock, relatively little is known about the biochemical mechanisms involved in LPS-induced events, e.g., TNF and IL-1 release, although an amplification system is suggested given that nanogram quantities of LPS can produce severe toxicity in animals. Most amplification pathways involve receptors and various enzyme cascades, thus allowing for several points of antagonism within the system. Although certain steps in LPS action are known, such as the stimulation of phosphoinositide hydrolysis, a transient increase in intracellular $Ca^{++}$ levels, and the activation of protein kinase C and phospholipase $A_2$, the lack of specific information on the cellular mechanisms involved in LPS action has impeded the development of therapeutic agents for preventing endotoxin shock.

Macrophages are particularly important cells in LPS-mediated TNF-α, IL-1, and IL-6 release. Although a detailed understanding of the cellular and biochemical processes through which LPS activates macrophages is unknown several lines of indirect evidence suggest that G-proteins might be involved in LPS action, which would be consistent with a receptor-linked cellular amplification pathway. Our finding that LPS stimulates a macrophage membrane-associated GTPase, an activity that is a hallmark of G-protein involvement, further supports a role for G-proteins in endotoxicity.

In our earlier application, we disclosed an assay for identifying compounds that inhibit the release of endotoxic shock mediators, such as TNF, by measuring the compounds ability to inhibit LPS-induced GTPase in an in vitro assay.

The assay basically comprises testing candidate compounds to determine if they are effective in blocking LPS-induced GTPase activity in macrophage membranes in vitro. Because previous studies suggested that a G-protein (a GTP-binding protein that becomes active when compounds bind to receptor and cause the G-protein to activate other cellular effector molecules) may participate in LPS action, we evaluated the effects of LPS on GTPase activity in membranes isolated from a macrophage (RAW 264.7) cell line. (G-proteins cause hydrolysis of GTP, hence, they are GTPases.) We found that LPS induced substantial GTPase activation (200–300% above basal), and kinetic analyses indicated that the maximal LPS-stimulated increase in velocity is observed within 15 min, that it is a low $K_m$ (GTP) activity, that it can be enhanced by ammonium sulfate, and that it appears to be pertussis toxin-insensitive.

Moreover, we found the LPS-enhanced GTPase activity was not antagonized by phosphatase/ATPase inhibitors such as p-nitrophenyl-phosphate, ouabain, bafilomycin or N-ethyl-maleimide, and in fact was potentiated by the addition of ATP or ADP. We found a synergistic effect on GTPase activity when both LPS and ATP or ADP are added to the macrophage assay. These data suggest that LPS may modulate the coupling between GTPase and a purinoreceptor, which is a class of cell surface hormone receptors that can bind ATP, ADP or related adenine nucleotides, and can serve to regulate cellular function via effects on selective G-proteins.

We also found that the LPS precursor, lipid X, which can reduce the lethal effects of LPS endotoxin, caused a dose-dependent inhibition of the LPS-mediated stimulation of GTPase activity. Half-maximal inhibition was seen at the same ratio of lipid X to LPS known to be effective in preventing endotoxin effects in vivo, i.e. at a one to one weight ratio. These effects are specific because other phospholipids, detergents and glycosides neither stimulated basal GTPase activity nor inhibited LPS-induced GTPase activity. Also, other studies showed that GTPase activity was not due to ATPase or to guanylate cycle activities.

In our earlier application we also disclosed our discovery that 2-chloro-ATP blocks both LPS-induced GTPase activity in RAW 2647 macrophages which provides additional evidence that GTPase is a determinative pathway for mediating endotoxicity.

Obviously, it would be advantageous to have compounds that could be useful as therapeutic agents in methods to prevent endotoxin shock. It also would be useful to have compounds which inhibit the release of tumor necrosis factor (TNF) and interleukin-1 (IL-1).

BRIEF SUMMARY OF THE INVENTION

It is an object of the present invention to disclose compounds which are useful in methods to prevent endotoxin shock.

It is an object to disclose methods of treatment of mammals to protect them from the deleterious effects of Gram-negative endotoxins and to inhibit the release of TNF and IL-1, which comprise administering to the mammals safe and effective amounts of compounds of the present invention.

The compounds which are useful to prevent or inhibit the lethal effects of endotoxin may be represented by the following formula:

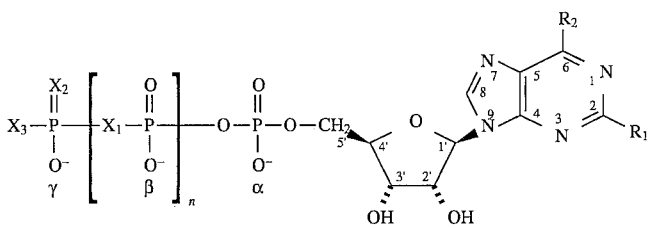

in which $X_1$ is a hydroxylation preventing group, such as —O—, —NH— or —CH$_2$—; $X_2$ is =O or =S; $X_3$ is —OH or —F; $R_1$ is a halogen or halogen-containing group, such as Cl—, or F— or CCl$_3$—; $R_2$ is —H, —CL, —F, —OH, =O, lower alkyl of 1 to 4 carbon atoms, —NH$_3$, —NH(CH$_3$), —N(lower alkyl)$_2$, —NHCOOCH$_3$, =S, —SH, —SCH$_3$ or —SO$_3$—; and n is 0 or 1. When n is 0, the compounds are diphosphates.

The compounds of Formula I in which $R_2$ is other than —NH$_2$ are believed to be novel compounds.

The methods of treatment of the present invention comprise administering to mammals to be protected from the deleterious effects of endotoxin (LPS) safe and effective amounts of compounds of Formula I.

The foregoing and other objects and advantages of the present invention will be apparent to those skilled in the art from the description of the preferred embodiment.

DESCRIPTION OF THE PREFERRED EMBODIMENT

In the preferred practice of the present invention, a compound of Formula I is administered to an animal in a safe and effective amount to protect it from the toxic effects of Gram-negative endotoxin. The preferred compound is 2-chloro-ATP (2-Cl-ATP) and the preferred route of administration is intravenously.

We discovered that 2-chloro-ATP is useful for inhibiting or preventing the lethal effects of endotoxin as a result of studying LPS-stimulated GTPase activity. During the course of studying LPS-stimulated GTPase activity, we first made the unexpected observation that ATP greatly enhanced the LPS-stimulation of macrophage membrane GTPase activity. Because ATP is an agonist for several purine nucleotide receptors that are coupled to G-proteins, and because ATP is released from the adrenal gland and other cells during inflammation, we initiated several studies to examine the possible linkage of macrophage purinoreceptors to the LPS-responsive GTPase activity and to LPS-induced death.

To define more clearly the relationship between adenine nucleotides and LPS, the activity of various purines was tested in the GTPase assay of our earlier application using macrophage membranes. Although ATP, ATPTS, ADP, and AMPPNP caused modest to little activation of GTPase activity in the absence of LPS, and LPS alone induced only a small activation of GTPase activity, the addition of LPS together with these purines triggered a synergistic increase (3–7-fold) in GTPase activity. The stimulation of basal GTPase activity by low levels of ATP and ADP suggested the presence of G-protein coupled purinoreceptors in these membranes. In addition, the activity of ATPTS and AMMP-PNP further supported the action of purinoreceptors over a phosphoryl donor activity, as these ATP analogs are poorly or non-hydrolyzable. The inhibition of GTPase at very high levels of ATP and ADP is likely to be due to competitive inhibition versus GTP for the GTPase. In contrast to ADP and the ATP analogs, the compounds, adenosine, AMP, NAD and theophylline failed to stimulate basal GTPase activity or synergize with LPS.

We discovered that 2-chloro-ATP (2-Cl-ATP) enhances the basal GTPase activity, but not the LPS-stimulated GTPase activity.

While these in vitro results were provocative, the antagonistic activity of 2-Cl-ATP needed to be assessed in an in vivo model of endotoxemia. In this regard, it can be seen in Table 1 that the lethal effects of endotoxin in mice were blocked by 2-Cl-ATP.

TABLE 1

Survival of Mice After Injection of LPS and a Second Injection of 2-chloro-ATP
All animals were given an initial injection of 600 μg LPS.
The 2-chloro-ATP given as the second injection was dissolved in saline solution. Average weight of mice was 19.5 g.

| Second Injection | Number of Mice Surviving After 72 Hours |
|---|---|
| Saline | 0/6 (0%) |
| 10 μg 2-chloro-ATP | 4/6 (67%) |
| 100 μg 2-chloro-ATP | 5/6 (83%) |
| 1 mg 2-chloro-ATP | 1/6 (17%) |

These data suggest that purinoreceptors are involved in the release of mediators during endotoxemia. This hypothesis also is supported by the observation that ATP and other purines are released from host cells during inflammation. In terms of the mechanism of interaction between LPS and purine nucleotides, several points along a signal transduction pathway are possible. For example, LPS might interact with a purinoreceptor(s) directly, with the G-protein(s) that is linked to a specific purinoreceptor(s), or with regulatory proteins that alter G-protein or receptor function. The concept that LPS interacts with a G-protein directly has theoretical support from the known binding of other lipids to G-proteins. Moreover, if LPS is internalized and acts by association with an intracellular protein (such as a G-protein), then the various macrophage surface proteins that bind LPS may act as transporters. This would explain the necessity for these binding proteins in LPS action, and why cells without an LPS transporter, which could not concentrate LPS intracellularly, would not be LPS responsive.

It remains to be determined if 2-Cl-ATP acts by competitive inhibition versus active purines such as ADP and ATP, or whether it modulates a specific ATP/ADP purinoreceptor by a separate class of purinoreceptor, or if it stimulates a negative regulatory pathway for TNF-α and IL-1 release. Ultimately, the purification of the components in the LPS-stimulated adenine nucleotide-regulated GTPase activity will be required to define the mechanism more clearly. Nevertheless, a novel approach for the treatment of endotoxemia is provided by the basic observations that purinoreceptors are important for endotoxin action and that a purine analog can prevent endotoxic death in mice.

Some of the 2-halo-adenosine-5'triphosphates, are known compounds. However, until our discovery it was not known that they could be useful in methods to inhibit or prevent the deleterious effects of endotoxin.

The compounds represented by Formula I may be prepared by known chemical procedures. For example, a method of preparing the 2-chloro derivatives is disclosed in Gough et al., *Journal of Medicinal Chemistry*, 1973, Vol. 6, No. 10, pages 1188–1190; a method of preparing the 2-fluoro derivatives is disclosed in Baldo et al., *Canadian J. Biochem*, Cell. Biol., Vol. 61, 1983, pp. 115–119; a method of preparing the triphosphates is disclosed in Moffatt, *Canadian Journal of Chemistry*, Vol. 42 (1964), pp. 599 to 604; and methods of effecting ring nitrogen substitution, substitution at exocyclic groups, making modified phosphate groups, synthesizing phosphate esters and synthesizing nucleoside polyphosphates are disclosed by Scheit in his text *Nucleotide Analogs*, a Wiley-Interscience Publication, John Wiley and Sons.

EXPERIMENTAL WORK

1. GTPase Assay

The preferred assay is comparable to that described by Cassel et al., Biochem, Biophys. Acta 452,538–551 (1976), and Neer et al., J. Biol. Chem. 259, 14222–14229 (1984), with two main exceptions: (1) We add ammonium sulfate because we found that although 300 μg LPS/ml increased GTPase activity by~30% in the absence of ammonium sulfate, in the presence of an optimal amount of ammonium sulfate (250 mM), the LPS-induced GTPase activity was nearly 3-fold above the reduced basal rate. Under these conditions, GTPase activation was evident at 100 μg LPS/ml (roughly 6 μM assuming an average MW 8 17,000 kDa), and the maximal effect was seen by 300 μg/ml LPS. (2) To show adenosine nucleotide synergism with LPS-stimulated GTPase activity, either 10 μM ATP or 30 μM ADP replace the 0.1 mM ATP and 0.2 mM AMPPNP of the standard assay described by Cassel et al. and Neer et al.

In the assay, a candidate compound (0.001–1000 μM) is dissolved or suspended in 100 μl of a reaction buffer containing 20 mM HEPES (pH 7.4), 0.01 mM ATP or 0.03 mM ADP, membranes isolated from RAW 264.7 cells, 2μM γ-$^{32}$P-GTP (3–9 X $10^3$cpm/pmol), 5 mM MgCl$_2$, 18 μM LPS (based on an estimated MW of 17,000 kDa for *E. coli* 0111:B4 endotoxin), and 250 mM ammonium sulfate. The reaction is initiated by the addition of the γ-$^{32}$P-GTP and the mixture incubated at 30°–37° C. for 15 to 30 minutes. The reaction is terminated by the addition of 500 μl of 5% trichloroacetic acid and 500 μl of 0.1gm/ml acid-activated charcoal in 5% trichloroacetic acid. The samples are centrifuged at 14,000xg for 10 minutes, and a 550 μl aliquot of the supernatant is removed for scintillation counting. The supernatant will contain the released $^{32}$Pi. The extent of GTPase inhibition is measured by the decrease in the amount of $^{32}$Pi released from γ-$^{32}$P-GTP. Appropriate controls include mixtures with one of the following omitted: (i) test compound, (ii) endotoxin, and (iii) ATP, ADP or AMPPNP.

The macrophage-like murine cell line RAW 264.7 is cultured using RPMI 1640 medium supplemented with 10% fetal calf serum (FCS) containing<0.1 ng/ml LPS. The membranes are resuspended in 20 mM HEPES (pH 7.4), 1 mM dithiothreitol, 1 mM EDTA and 10 μg leupeptin/ml. Aliquots are stored at −70° C. until assayed.

2. Effect of ATP

To further characterize the specificity of the LPS-stimulated GTPase, we first assayed its activity in the absence of any other nucleotides, and then compared this response to that found in reactions containing various ATPase/nucleotidase inhibitors. If the GTPase activity is due to a generalized increase in nucleotidase-like activities, one would expect that the inclusion of these inhibitors would attenuate the LPS-stimulated activity. Release of $^{32}$Pi from γ-$^{32}$P-GTP would be predicted to be unaffected or even enhanced (more non-specific substrate hydrolysis) in the absence of these agents. Surprisingly, we observed that in the absence of any added adenine nucleotides, there was very little detectable LPS-enhanced GTPase activity. However, when either ATP, ADP or the non-hydrolyzable ATP analog AMPPNP was included in the incubation, there was a pronounced increase in LPS-stimulated GTPase activity. Moreover, the addition of the ATPase inhibitors ouabain, bafilomycin and N-ethylmaleimide did not block LPS-stimulated GTPase activity in the presence of ADP. Conversely, as expected, the very general phosphoryl transferase inhibitor, sodium orthovanadate, did block LPS activation.

Because the above inhibitor studies indicated a maximum LPS-stimulated GTPase activity in the presence of ATP and ATP analogs, we investigated this interaction by measuring the ATP-dependence of the GTPase activity in macrophage membranes in the presence and absence of an optimal dose of LPS. ATP alone exhibited a biphasic stimulation of GTPase activity, with the maximum effect being observed around 1–10 μM. This stimulation by ATP may be due to the action of purinergic receptors, i.e., the adenosine and ATP receptors which are well-characterized to be coupled to various G-proteins.

When ATP and LPS are added together, there is a striking stimulation of GTPase activity at 1–10 μM ATP which is much greater than that seen with ATP or LPS alone. This synergistic stimulation by ATP plus LPS is also biphasic, with the inhibition of GTPase activity observed at very high ATP levels probably resulting from competitive or ionic effects. These data suggest that LPS may interact in some fashion with the purinergic receptor signal transduction pathway and that the LPS-mediated GTPase activation is not the result of a non-specific ATPase or other nucleotidase activity.

To assess whether the LPS/ATP-enhanced GTPase is a "low $K_m$" form, which would be expected for a variety of large and small MW G-proteins, as well as for various GAP and ARF-like proteins, as opposed to a "high $K_m$" form, such as a phosphatase, we assayed the GTPase activity using 0.2 and 50 μM GTP essentially as described previously. In view of the interactive effects of LPS and ATP, we measured high and low $K_m$ GTPase in the absence of added ATP, as well as in the presence of a maximal activating dose of ATP (10 μM), and compared these results to those obtained using our standard assay conditions (2 μM GTP, 0.1 mM ATP, 0.2 mM AMPPNP). The LPS and ATP stimulated a low $K_m$ GTPase activity by ~30% and 70%, respectively, when added individually. This stimulation of low $K_m$ activity was slightly greater than that estimated using the standard assay conditions. In addition, the combined effects of LPS and ATP on GTPase activity also appeared to represent an influence on a low $K_m$ component, with the stimulation calculated for the low $K_m$ activity (228% of basal activity) being comparable to the stimulation (208% of basal activity) measured using our standard assay conditions. In sum, the LPS-stimulated GTPase activity appears specific for GTP, it exhibits a low $K_m$ (GTP), and it is insensitive to various ATPase inhibitors. The LPS stimulation of GTPase activity is enhanced by adenine nucleotides.

3. Effect of ATP Analogs

In the presence of LPS, ATP results in a three-fold increase in activity of the GTPase. Therefore, we examined the ability of ATP analogs to stimulate LPS-enhanced GTPase activity. In dose-response studies, the relative abilities of purines to stimulate LPS-enhanced GTPase were: ATP>ATPγS>ADP>AMPPNP>> β, γ methylene ATP>2-Cl-ATP.

AMP and adenosine at 100 μM were ineffective, while ATP was active at 1 μM. This is the general order of purine agonist activity for the P2-type purinoreceptor (P2-R). Also, IBMX, an antagonist of both types of P1 purinoreceptors, but with no effect on P2 receptors, did not alter the LPS activation of the GTPase. (There are no known P2x, P2y, or P2z receptor antagonists currently available, while ATP is a P2t inhibitor, but an agonist in our system.) Of interest, one of the Gi-like proteins linked to the P2-purinoreceptors is resistant to pertussis toxin inactivation which is consistent with our results. Also, P2-receptor activation is linked to inositol phosphate breakdown in HL60 cells. Finally, LPS has been reported to decrease purine exonucleotidase activity of glomerular endothelial cells, as assessed by enzyme cytochemistry. These results open the possibility that the P2-R may be involved is some LPS-mediated activities. For example, since ATP infusion is known to result in shock, one might hypothesize the following events: LPS sensitizes P2-R to ATP via enhanced ligand binding to the P2-R or increased G-protein interaction with P2-R, and LPS might decrease intravascular breakdown ATP and ADP. Thus, in the presence of LPS, normal concentrations of ATP might result in shock and death.

Examination of the dose-response curves of ATP and ATP analogs, show that 2-chloro-ATP (2-Cl-ATP) has no stimulatory effect on LPS-induced GTPase activity. Because 2-Cl-ATP is an excellent ligand for two of the subtypes of the P2-R (P2y- and P2z-receptors), we hypothesized that 2-Cl-ATP might be an antagonist. We found that 2-Cl-ATP did antagonize the stimulatory effects of ATP on LPS-inducible GTPase activity. When increasing amounts of 2-Cl-ATP (0–100 μM) were added to the macrophage assay system, the activity of the LPS-enhanced GTPase decreased.

Although the foregoing tests all involved the use of 2-chloro-ATP, the administration of other compounds of Formula I which are identified as inhibiting GTPase, also can be useful to ameliorate pathological conditions created by many endotoxin-induced diseases.

The need for additional compounds that will prevent endotoxin shock is great because endotoxin or lipopolysaccharide (LPS) is highly toxic. For example, the LD50 for the lipopolysaccharide in sheep is about 10–20 μg/kg (intravenous), while in mice it is about 5 mg/kg. In sheep (and probably also in humans) lipopolysaccharide causes death by promoting the release of mediators that trigger pulmonary hypertension, pulmonary edema, and peripheral vascular collapse. Death usually occurs within 8 to 48 hours after injection of lipopolysaccharide or lipid A. Occasionally, death will occur at 1–2 weeks. This is usually the result of disseminated intravascular coagulopathy leading to renal cortical necrosis and uremic death.

Previous work on the lethal endotoxicity of LPS showed that only limited prevention of the complications of injection of this material could be achieved through the administration of glucocorticoids, prostaglandins, naloxone, pressors, fluid replacement therapy or anti-LPS antibodies. In addition, all existing therapies against LPS lethality are dependent upon their being given prior to or very shortly after the administration of the LPS challenge.

Furthermore, protection with such compounds might be obtained even after the signs and symptoms of endotoxemia had been developed. This is an extremely important therapeutic consideration, since the signs and symptoms of a disease must almost always manifest before therapy is initiated. Although the mechanism(s) by which protective compounds inhibit LPS-inducible GTPase activity in the assay remain unknown, the data fit best for agents interrupting a signal transduction pathway involving purinoreceptors that are linked to an endotoxin-responsive G-protein (i.e., GTPase) that ultimately leads to the release of IL-1 and TNF by macrophages.

The pretreatment of mammals, such as humans, sheep or mice, with a compound of Formula I which can block adenine nucleotide-stimulated GTPase activity should make the mammal resistant to the lethal effects of Gram-negative endotoxin.

We also envision that treatment of a mammal after the symptoms of endotoxin shock appear will lessen disease symptoms. Of note, current therapies are aimed at killing the gram negative bacteria (antibiotics) and at neutralizing circulating endotoxin (anti-endotoxin antibodies). However, these therapies have the disadvantages of releasing more endotoxin and having no effect on endotoxin already internalized into cells. This last disadvantage is clinically very relevant because the signs and symptoms of endotoxemia are often not manifest until 1.5–3 hours after the endotoxin is released into the patient, thus rendering anti-endotoxin antibodies less effective. The apparent antagonism between the compounds identified as GTPase inhibitors and endotoxin can have useful applications in clinical situations and disease states that are caused by endotoxin, such as Gram-negative sepsis following surgery in humans and animals, bovine or porcine mastitis, and other endotoxin-related veterinary diseases listed in Tables 2 and 3.

While LPS activation of macrophage-purinoreceptors is a specific case of macrophage activation, this may represent a more general case for macrophage activation. For example, endotoxin (LPS) may substitute for naturally occurring mammalian lipids that are released during tissue damage along with intracellular ATP or ADP. This combination of lipid plus purine might then activate macrophages. Hence, 2-Cl-ATP and other purinoreceptor-active derivatives might block macrophage activation seen in a number of other pathophysiological conditions. Thus, several other disease states wherein the compounds of Formula I might be useful are listed in Table 4.

The compounds of Formula I may be introduced into the circulation of an animal by oral, intravenous, intraperitoneal or intramuscular routes, to induce a state of relative resistance to the deleterious effect of lipopolysaccharide. When thus employed, the compounds may be administered in the form of parenteral solutions containing the selected protective compound, in a sterile liquid suitable for intravenous or other administration. The exact route, dose, and administration interval of the active compounds will vary with the size and weight of the animal, and the species, and the desired level of protection. However, in general the dosage will be similar to that for 2-chloro-ATP which is about 1 mg/kg to about 50 mg/kg.

Table 2

Pet Animal and Livestock Endotoxemias and Other Pathophysiological Entities with High Probability of Being Prevented or Treated by Administration of Compounds Which Inhibit GTPase are the following:
Mammalian
  Gastritis
  Digestive disorders of the rumen including -
    Bloat
    Simple indigestion
    Grain overload
  Abomasal disorders
    Displacement/torsion of the abomasum
    Impaction of the abomasum
  Edema disease of swine
  Colibacillosis of weaned pigs
  Enteritis of small and large animals
  Small intestinal obstruction
  Colon impaction of small animals
  Intussusceptions
  Intestinal torsion and volvulus
  Impaction of the large intestine
  Intestinal foreign bodies
  Intestinal incarceration
  Colitis
  Colic in horses
  Salmonellosis/typhoid fever
  Colibacillosis
  Diarrhea of newborn animals
  Chronic diarrhea
  Toxicosis of chemical and plant origins
  Gastrointestinal parasites including coccidiosis and sarcosporidiosis
  Malabosorbtion syndrome
  Hemorrhagic bowel syndrome
  All other syndromes which cause loss of gastrointestinal homogeneity such as abrupt changes in diet or feeding regimen in mammalian species
  Infectious necrotic hepatitis
  Bacillary hemoglobinuria
  Hepatitis of parasitic etiology
  Hepatic distomatosis
  Chemical hepatosis from protein deficiencies, vitamin E deficiency, pyrrolizidine alkaloids, from parasites during migrations, infectious and pyogenic diseases, metabolic diseases, copper poisonings
Avian syndromes
  Enteritis of infectious or nutritional origin;
    infectious etiology is intended to include bacterial, viral and parasitic etiologies.
  Hepatitis of infectious or parasitic etiologies
  Coccidiosis, hexamitiasis, histomoniasis Table 3

Human Diseases with High Probability of Being Prevented or Treated by the Administration of Compounds Which Inhibit GTPase are the following:
(1) Gram-negative sepsis
(2) Endotoxemia from burn wounds, pyelonephritis, peritonitis, cellulitis, abscess, prostatitis, genitourinary tract infections, mastitis, pneumonia, empyema, cholecystitis, bacterial hepatitis, meningococcemia, gonococcemia, colitis, toxic megacolon, meningitis, etc.
(3) Loss of G.I. mucosal barrier, e.g. trauma, drug-induced mucositis.

Table 4

Other non-endotoxin uses for purinoreceptor-inhibitors:
  Pancreatitic
  Myocardial infarction
  Crush Trauma
  Burns (chemical and thermal)
  Vasculitis
  Drug toxicities involving macrophage activation
  Toxic shock syndrome
  Enterotoxin
  Overwhelming Viremia
  Viral pneumonia
  Immune complex diseases
  Aspiration pneumonia
  Drowning
  Inhaled toxins or irritants
  Shock lung
  Reperfusion injuries It will be apparent to those skilled in the art that a number of changes and modifications can be made without departing from the spirit and scope of the present invention. Therefore, it is intended that the invention only be limited by the claims.

The embodiments of the invention in which an exclusive property or privilege is claimed are the following:

1. A method of reducing the damage caused by entotoxin in a mammal comprising administering to said mammal a therapeutic amount of a compound of the following formula:

$$X_3 - \underset{\underset{\text{OH}}{\underset{|}{P}}}{\overset{\overset{X_2}{\overset{\|}{}}}{}} - \left[ X_1 - \underset{\underset{\text{OH}}{\underset{|}{P}}}{\overset{\overset{O}{\overset{\|}{}}}{}} \right]_n - O - \underset{\underset{\text{OH}}{\underset{|}{P}}}{\overset{\overset{O}{\overset{\|}{}}}{}} - O -$$

$$\gamma \qquad \beta \qquad \alpha$$

-continued
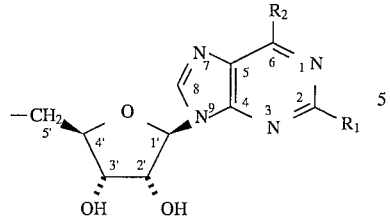
wherein
$X_1$ is —O—, —NH—, or —CH$_2$—;
$X_2$ is —OH, —NH$_2$, or —CH$_3$;
$X_3$ is —OH;
$R_1$ is a halogen;
$R_2$ is is —NH$_2$, —HN(CH$_3$), or —NH(lower alkyl)$_2$; and
n is 0 or 1.
2. The method of claim 1 wherein $R_1$ is chloro.
3. The method of claim 1 wherein said compound is 2-chloro-adenosine-5'-triphosphate.
* * * * *